United States Patent
Yanez et al.

(10) Patent No.: US 6,656,215 B1
(45) Date of Patent: Dec. 2, 2003

(54) STENT GRAFT HAVING AN IMPROVED MEANS FOR ATTACHING A STENT TO A GRAFT

(75) Inventors: Andrew Yanez, Miami, FL (US); Frank Butaric, Pembroke Pines, FL (US); Marc Ramer, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 134 days.

(21) Appl. No.: 09/714,080

(22) Filed: Nov. 16, 2000

(51) Int. Cl.⁷ .................................................. A61F 2/06
(52) U.S. Cl. ...................................... 623/1.13; 623/1.15
(58) Field of Search ............................... 623/1.13, 1.15; 606/75, 219; 227/902, 15, 16

(56) References Cited

U.S. PATENT DOCUMENTS

| | | | | |
|---|---|---|---|---|
| 3,598,299 A | * | 8/1971 | Johnson | 227/144 |
| 4,317,451 A | | 3/1982 | Cerwin et al. | 128/325 |
| 4,532,927 A | * | 8/1985 | Miksza, Jr. | 128/334 C |
| 4,553,545 A | | 11/1985 | Maass et al. | 128/341 |
| 4,580,568 A | | 4/1986 | Gianturco | 128/345 |
| 4,627,437 A | * | 12/1986 | Bedi et al. | 128/334 C |
| 4,655,771 A | | 4/1987 | Wallsten | 623/1 |
| 4,665,906 A | | 5/1987 | Jervis | 128/92 |
| 4,681,110 A | | 7/1987 | Wiktor | 128/343 |
| 4,719,917 A | * | 1/1988 | Barrows et al. | 128/334 R |
| 4,732,152 A | | 3/1988 | Wallsten et al. | 128/343 |
| 4,733,665 A | | 3/1988 | Palmaz | 128/343 |
| 4,739,762 A | | 4/1988 | Palmaz | 128/343 |
| 4,776,337 A | | 10/1988 | Palmaz | 128/343 |
| 4,784,137 A | | 11/1988 | Kulik et al. | 128/334 |
| 4,875,480 A | | 10/1989 | Imbert | 128/343 |
| 4,907,336 A | | 3/1990 | Gianturco | 29/515 |
| 4,950,227 A | | 8/1990 | Savin et al. | 604/8 |
| 4,990,151 A | | 2/1991 | Wallsten | 606/108 |

(List continued on next page.)

FOREIGN PATENT DOCUMENTS

| | | | |
|---|---|---|---|
| EP | 0657147 A2 | 10/1994 | |
| EP | 0 657 147 A2 | 10/1994 | A61F/2/06 |
| EP | 783 873 | 7/1997 | A61F/2/06 |
| EP | 880 948 | 2/1998 | A61F/2/06 |
| EP | 1000590 | 5/2000 | 623/1 |
| FR | 2 743 293 | 1/1996 | A61F/2/06 |
| JP | 5524095 A | 2/1980 | |
| WO | WO 87/04935 | 8/1987 | A61M/29/00 |
| WO | 8704935 A1 | 8/1987 | |
| WO | 9516406 A1 | 6/1995 | |
| WO | WO 95/16406 | 6/1995 | A61F/2/06 |
| WO | 9521592 A1 | 8/1995 | |
| WO | WO 95/21592 | 8/1995 | A61F/2/06 |
| WO | WO 97/33532 | 9/1997 | A61F/2/06 |
| WO | 9807389 A1 | 2/1998 | |
| WO | WO 98/07389 | 2/1998 | A61F/2/06 |
| WO | 9911199 A1 | 3/1999 | |
| WO | WO 99/11199 | 3/1999 | A61F/2/06 |

*Primary Examiner*—Bruce Snow
*Assistant Examiner*—Cheryl Miller

(57) ABSTRACT

A stent-graft for insertion into a body lumen, such as a blood vessel, is utilized in order to repair such lumen. The stent-graft includes a substantially cylindrical hollow expandable stent comprising a plurality of interconnected struts. The stent has a distal end and a proximal end, and an interior surface and an exterior surface. At least one strut of the stent has first and second apertures extending therethrough from the interior surface to the exterior surface. The stent-graft also includes a graft member covering a predetermined portion of least one of the interior surface and the exterior surface of the stent. In addition, the stent-graft further includes a staple for attaching the graft member to the stent. The staple has a crown and two legs extending therefrom. At least one of the legs of the staple extends through the graft material and through the first aperture. Both of the legs are bent inwardly towards said crown such that they evert back and extend through the second aperture.

19 Claims, 17 Drawing Sheets

U.S. PATENT DOCUMENTS

| | | | | |
|---|---|---|---|---|
| 5,026,337 | A | 6/1991 | Miura et al. | 475/283 |
| 5,026,377 | A | 6/1991 | Burton | |
| 5,045,072 | A | 9/1991 | Castillo et al. | 604/280 |
| 5,159,920 | A | 11/1992 | Condon et al. | 128/6 |
| 5,209,756 | A * | 5/1993 | Seedhom et al. | 606/151 |
| 5,219,355 | A | 6/1993 | Parodi et al. | 606/191 |
| 5,304,197 | A | 4/1994 | Pinchuk et al. | 606/194 |
| 5,316,023 | A | 5/1994 | Palmaz et al. | 128/898 |
| 5,318,535 | A | 6/1994 | Miraki | 604/102 |
| 5,342,395 | A * | 8/1994 | Jarrett et al. | 606/219 |
| 5,360,443 | A | 11/1994 | Barone et al. | 623/1 |
| 5,411,507 | A | 5/1995 | Heckele | 606/108 |
| 5,476,506 | A | 12/1995 | Lunn | 623/1 |
| 5,480,423 | A | 1/1996 | Ravenscroft et al. | 623/1 |
| 5,484,444 | A | 1/1996 | Brauschweiler et al. | 606/108 |
| 5,507,769 | A | 4/1996 | Marin et al. | 606/198 |
| 5,522,880 | A | 6/1996 | Barone et al. | 623/1 |
| 5,562,724 | A | 10/1996 | Vorwerk et al. | 623/1 |
| 5,571,170 | A | 11/1996 | Palmaz et al. | 623/1 |
| 5,571,171 | A | 11/1996 | Barone et al. | 623/1 |
| 5,571,173 | A | 11/1996 | Parodi | 623/1 |
| 5,578,071 | A | 11/1996 | Parodi | 623/1 |
| 5,578,072 | A | 11/1996 | Barone et al. | 623/1 |
| 5,591,229 | A | 1/1997 | Parodi | 623/1 |
| 5,628,788 | A | 5/1997 | Pinchuk | 623/1 |
| 5,632,763 | A | 5/1997 | Glastra | 606/194 |
| 5,639,278 | A | 6/1997 | Dereume et al. | 623/1 |
| 5,653,745 | A | 8/1997 | Trescony et al. | 623/1 |
| 5,676,696 | A | 10/1997 | Marcade | 623/1 |
| 5,683,449 | A | 11/1997 | Marcade | 623/1 |
| 5,693,084 | A | 12/1997 | Chuter | 623/1 |
| 5,702,418 | A | 12/1997 | Ravenscroft | 606/198 |
| 5,749,880 | A | 5/1998 | Banas et al. | 606/198 |
| 5,760,006 | A | 6/1998 | Shank et al. | 514/23 |
| 5,824,040 | A | 10/1998 | Cox et al. | 623/1 |
| 5,824,042 | A | 10/1998 | Lombardi et al. | 623/1 |
| 5,843,160 | A | 12/1998 | Rhodes | 623/1 |
| 5,855,598 | A | 1/1999 | Pinchuk | 623/1 |
| 5,915,615 | A * | 6/1999 | Bauer | 227/177.1 |
| 5,980,565 | A | 11/1999 | Jayaraman | 623/1 |
| 5,993,481 | A | 11/1999 | Marcade et al. | 623/1 |
| 6,039,749 | A | 3/2000 | Marin et al. | 606/198 |
| 6,070,589 | A | 6/2000 | Keith et al. | 128/898 |
| 6,071,307 | A * | 6/2000 | Rhee et al. | 623/1.13 |
| 6,193,745 | B1 * | 2/2001 | Fogarty et al. | 623/1.12 |
| 6,203,568 | B1 * | 3/2001 | Lombardi et al. | 623/1.13 |
| 6,254,632 | B1 * | 7/2001 | Wu et al. | 623/1.15 |
| 6,302,906 | B1 | 10/2001 | Goicoechea et al. | |
| 6,306,164 | B1 | 10/2001 | Kujawski | |
| 6,325,819 | B1 | 12/2001 | Pavenick et al. | |
| 6,361,557 | B1 * | 3/2002 | Gittings et al. | 623/1.13 |

* cited by examiner

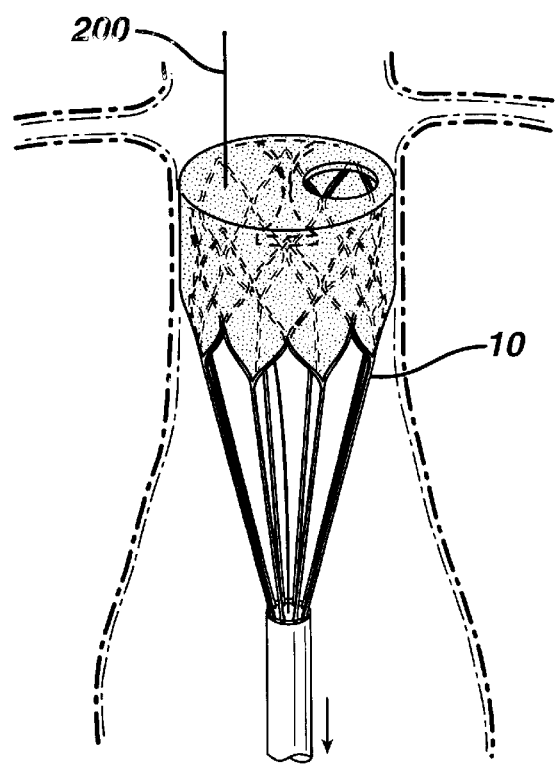
FIG. 24
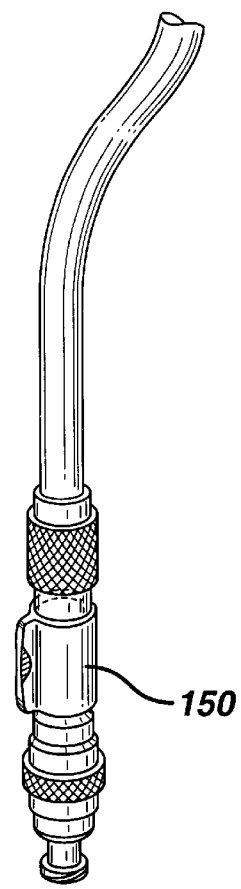

STENT GRAFT HAVING AN IMPROVED MEANS FOR ATTACHING A STENT TO A GRAFT

FIELD OF THE INVENTION

The present invention relates to percutaneously delivered stent-grafts for repairing abdominal aortic aneurysms.

BACKGROUND OF THE INVENTION

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm often arises in the infrarenal portion of the diseased aorta, for example, below the kidneys. When left untreated, the aneurysm will eventually cause rupture of the sac with ensuing fatal hemorrhaging in a very short time. High mortality associated with the rupture has led to the present state of the art and the trans-abdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of either DACRON®, TEFLON®, GORTEX®, or other suitable material.

To perform the surgical procedure requires exposure of the aorta through an abdominal incision, which can extend from the rib cage to the pubis. The aorta must be cross-clamped both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still relatively high. Although abdominal aortic aneurysms can be detected from routine examinations, the patient may not experience any pain from the condition. Thus, if the patient is not receiving routine examinations, it is possible that the aneurysm will progress to the rupture stage.

Disadvantages associated with the conventional, prior art surgery, in addition to the high mortality rate, are: the extended recovery period associated with the large surgical exposure in such open procedures; difficulties in suturing the graft, or tube, to the aorta; the loss of the existing thrombosis to support and reinforce the graft; the unsuitability of the surgery for many patients having abdominal aortic aneurysms; and the problems associated with performing the surgery on an emergency basis after the aneurysm has ruptured. As to the extent of recovery, a patient can expect to spend from 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is often difficult to perform the suturing step because of thrombosis present on the remaining portion of the aorta, and that remaining portion of the aorta wall may be friable, or easily crumbled.

Since the thrombosis is totally removed in the prior art surgery, the new graft does not have the benefit of the previously existing thrombosis therein, which could be utilized to support and reinforce the graft, were the graft to be able to be inserted within the existing thrombosis. Since many patients having abdominal aortic aneurysms have other chronic illnesses, such as heart, lung, liver, and/or kidney disease, coupled with the fact that many of these patients are older, these patients are not ideal candidates for such surgery, which is considered major surgery. Such patients have difficulties in surviving the operation. Lastly, once the aneurysm has ruptured, it is difficult to perform a conventional surgery on an expedited basis because of the extent of the surgery.

Accordingly, the prior art teaches various methods and apparatuses for repairing an abdominal aortic aneurysm which is believed to lower morbidity and mortality rate by not requiring an abdominal incision and general anesthesia, not requiring suturing the graft to the remaining aortic wall, and which permits the existing aortic wall and thrombosis therein to be retained to reinforce and support the aortic graft. An example of such a method and apparatus is given in U.S. Pat. No. 5,316,023 issued to Palmaz et al. on May 31, 1994; U.S. Pat. No. 5,360,443 issued to Barone et al. on Nov. 1, 1994; U.S. Pat. No. 5,578,071 issued to Parodi on Nov. 26, 1996; and U.S. Pat. No. 5,591,229 issued to Parodi on Jan. 7, 1997, all of which are hereby incorporated herein by reference.

Devices, such as the one shown in the above referenced Barone patent, use an improved method for repairing an abdominal aortic aneurysm in an aorta having two iliac arteries associated therewith. The device includes first and second tubes, preferably made from a variety of materials such as DACRON® and other polyester materials, TEFLON® (polytetrafluoroethylene), TEFLON® coated DACRON®, porous polyurethane, silicone, expanded polytetrafluoroethylene, and expanded polyurethane. It is preferred that all of the foregoing materials be porous to allow for an intimal layer to form on the tubes. Each of the tubes are connected to expandable and deformable tubular members, or stents. These stents can be similar in structure to those described in disclosed in U.S. Pat. No. 4,733,665 issued on Mar. 29, 1988; U.S. Pat. No. 4,739,762, issued on Apr. 26, 1988; and U.S. Pat. No. 4,776,337 issued on Oct. 11, 1988, all of the foregoing patents being in the name of Julio C. Palmaz, each of which is incorporated herein by reference. Each of the tube/stent structures are then disposed on the end of a balloon catheter. Either both tubes are inserted into the same femoral artery or one of the tubes is inserted into one femoral artery of the patient and the other tube is inserted into the other femoral artery of the patient. Thereafter the tubes are intraluminally delivered to the aorta, thereby disposing at least a portion of each tube within the abdominal aortic aneurysm. The balloons on the distal ends of the catheters are then expanded to expand and deform the tubular members, to force the tubular members radially outwardly into contact with the aorta and each other. This secures the tubular members and a least a portion of each tube within the aorta, whereby the tubes provide a bilateral fluid passageway through the abdominal aortic aneurysm.

While the above mentioned devices would seem to work well, there is a desire to improve upon the device. More particularly, there was a need to ensure that most of the blood flowing through the abdomen flows through the bilateral fluid passageways and not around them where it could cause further damage. The precursor stent gasket described in commonly assigned European Patent Application EP 0947179, filed on Mar. 29, 1999, European Patent Application EP 1000590 (A1), filed on Nov. 8, 1999, and pending U.S. patent application Ser. No. 09/404,660 filed on Sep. 24, 1999, the disclosures of which are hereby incorporated herein by reference, limits the amount of blood which could leak around the bilateral fluid passageways and into the aneurysm. The precursor stent gasket is positioned within the infrarenal neck, between an abdominal aortic aneurysm and the renal arteries, of a patient to assist in repairing the abdominal aortic aneurysm. The stent is designed to be coupled to the bilateral grafts for directing blood flow. The graft has a distal end for positioning distal to the aneurysm, and a proximal end for positioning proximal to the aneurysm. The precursor stent gasket includes a substantially cylindrical expandable member having a proximal end, a distal end and an interior. The stent gasket further includes a compressible gasket member located within the interior of the expandable member and attached thereto. The compressible member is substantially impervious to blood when in a compressed state and is coupled the graft. This is so the coupled device can direct blood flow through the graft, with the gasket member substantially preventing blood from flowing into the aneurysm.

While the above described devices are large improvements over the prior art, there has been a need for improvement. There has been a desire to have a better device for attaching the graft material to the grafts used in the above described devices. There has been a desire to have an improved stent gasket member for better attachment of the stent gasket member to aortic wall. There has been a desire to have a mechanism for ensuring that the stent gasket member is not prematurely deployed. There has been a desire to improve the design of the stent grafts to make them perform better. Lastly, there has been a desire to improve the grafts on the stent grafts themselves to make them perform better during deployment. The following described invention provides such an improved device.

SUMMARY OF THE INVENTION

In accordance with the present invention there is provided a stent graft for insertion into a body lumen, such as a blood vessel, in order to repair such lumen. The stent graft includes a substantially cylindrical hollow expandable stent comprising a plurality of interconnected struts. The stent has a distal end and a proximal end, and an interior surface and an exterior surface. At least one strut of the stent has first and second apertures extending therethrough from the interior surface to the exterior surface. The stent graft also includes a graft member covering a predetermined portion of least one of the interior surface and the exterior surface of the stent. In addition, the stent graft further includes a staple for attaching the graft member to the stent. The staple has a crown and two legs extending therefrom. At least one of the legs of the staple extends through the graft material and through the first aperture. Both of the legs are bent inwardly towards said crown such that they evert back and extend through the second aperture.

BRIEF DESCRIPTION OF DRAWINGS

The foregoing and other aspects of the present invention will best be appreciated with reference to the detailed description of the invention in conjunction with the accompanying drawings, wherein:

FIG. 24 is a view similar to that of FIG. 23 but showing the stent gasket partially deployed from its delivery system.

DETAILED DESCRIPTION OF THE INVENTION

One preferred use of the present invention is to treat abdominal aortic aneurysms. A better understanding of the present device and its use in treating abdominal aortic aneurysms will be achieved by reading the following description in conjunction with the above incorporated references. In addition, the terms cranial and distal, will refer to the direction towards the head of the patient, and the terms caudal or proximal will refer to the direction away from the head of the patient.

Figure 1:
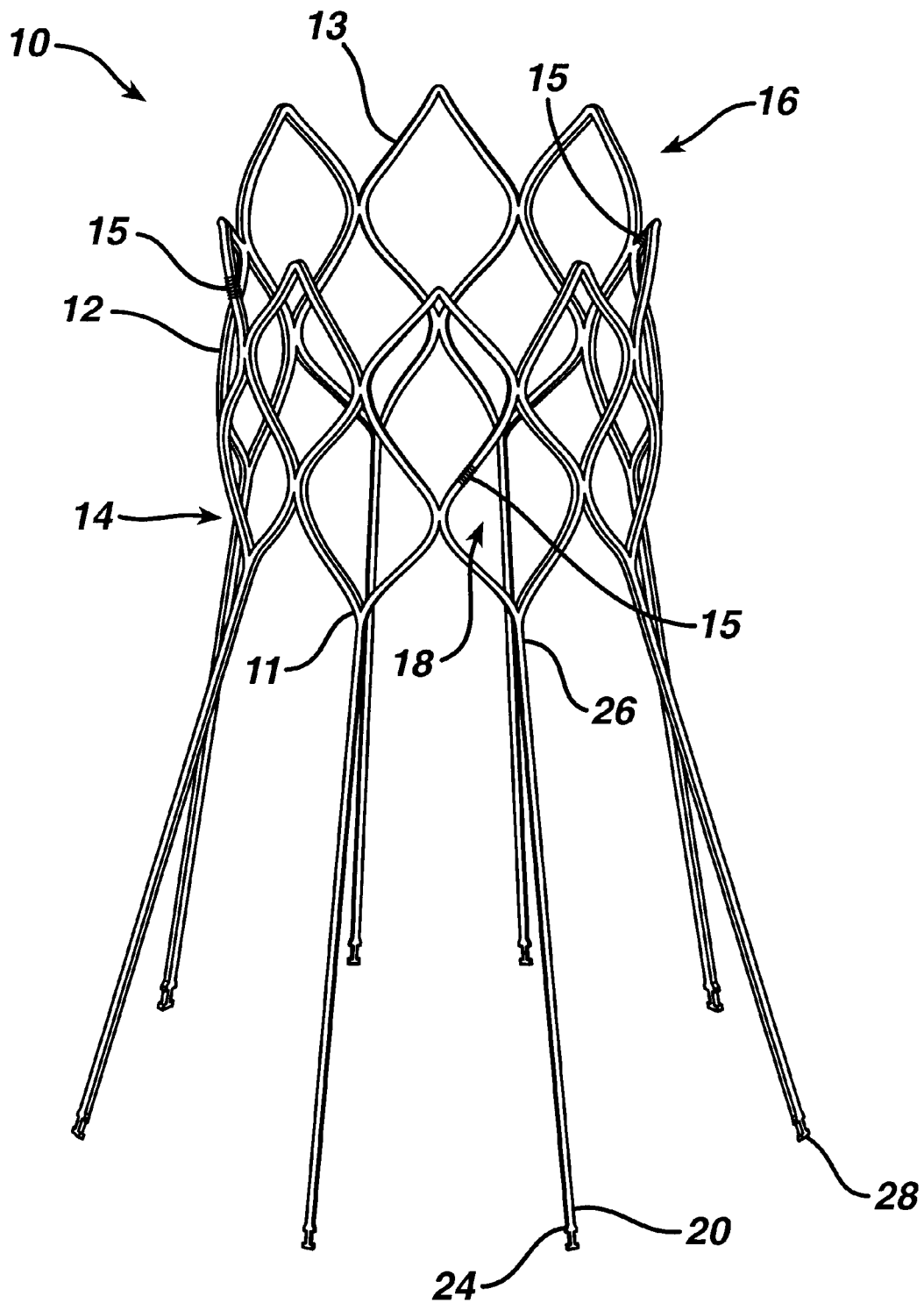
FIG. 1 is a perspective view of a precursor stent (shown without the gasket, in an expanded state) made in accordance with the present invention.

Referring now to the drawings wherein like numerals indicate the same element throughout the views, there is shown in FIG. 1 a precursor stent 10, shown in FIG. 1. As will be discussed below, precursor stent 10 is to be deployed within the infrarenal neck, between an abdominal aortic aneurysm and the renal arteries of a patient to assist in repairing the abdominal aortic aneurysm. The precursor stent is designed to be coupled to one or more stent-grafts for directing blood flow through the aneurysm. The precursor stent includes a substantially cylindrical self-expanding member 12 made from a plurality of interconnected struts. Self-expanding member 12 having two open ends, a proximal end 14, a distal end 16, and a longitudinal axis extending therebetween and an interior 18. The precursor stent further includes at least two, but preferably 8 as shown in FIG. 1, spaced apart longitudinal legs 20 each having proximal and distal ends 24 and 26 respectively. Preferably, there is a leg extending from each apex 11 of diamonds 13 (such diamonds being formed by the struts). The distal ends 26 of the legs are attached to the proximal end 14 of the self-expanding member 12, the legs extending proximally away from the self-expanding member. At least one, but preferably each leg includes a flange 28 adjacent its proximal end which, as is described in greater detail below, allows for the stent to be retrieved into its delivery apparatus after partial or full deployment of self-expanding member 12 so that it can be turned, or otherwise repositioned for proper alignment.

The self-expanding stents described herein are preferably made from superelastic Nickel Titanium alloys (Nitinol). Descriptions of medical devices which use such alloys can be found in U.S. Pat. No. 4,665,906 issued to Jervis on May 19, 1987, and European Patent Application EP 0928606 filed on Jan. 8, 1999, both of which are hereby incorporated herein by reference. Precursor stent 10 is preferably laser cut from a tubular piece of Nickel Titanium Alloy and thereafter treated so as to exhibit superelastic properties at body temperature. Precursor stent 10 is shown in the figures as being a diamond patterned stent, having approximately 8 diamonds, and when the stent is fully expanded the diamonds would have angles of 45–55 degrees at their distal and proximal ends. However, precursor stent 10 can take on many different patterns or configurations.

Figure 19:
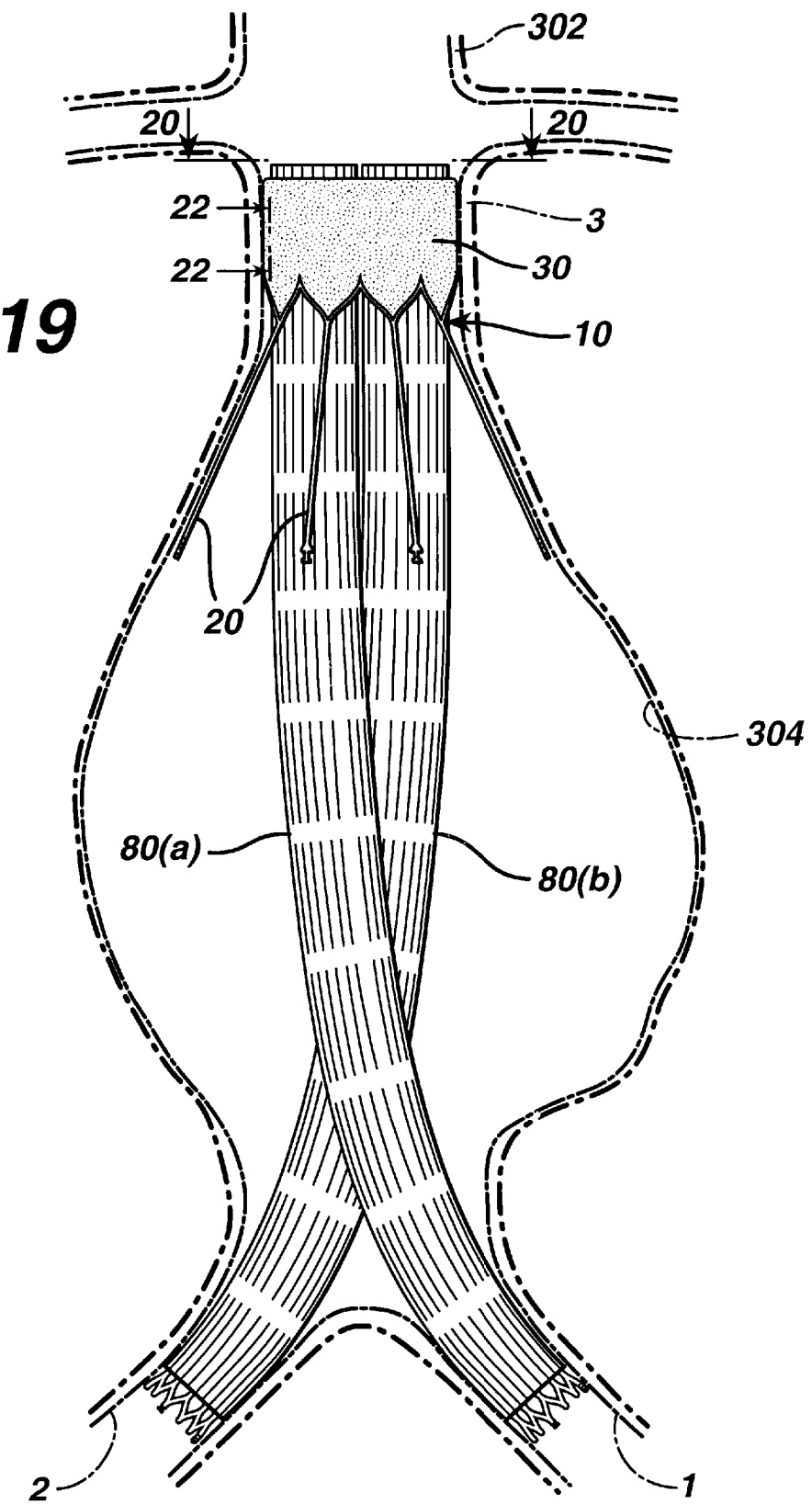
FIG. 19 is an elevational view of a fully deployed abdominal aortic repair system made in accordance with the present invention.

In one embodiment of precursor stent 10, shown in most of the figures but removed from FIG. 1 for clarity, precursor stent 10 further includes a gasket member 30 (thereby forming a stent gasket or stent-graft). This feature can be better understood by referring to FIGS. 2 and 3. As seen from those figures, precursor stent 10 further includes a gasket member 30. Gasket member 30 surrounds the self-expanding member 12 and can be located along the interior of self-expanding member 12, the exterior of self-expanding member 12 or both. The gasket member helps impede any blood trying to flow around the stent-grafts, described below, after they have been inserted (as shown in FIG. 19) and from flowing around the precursor stent itself. For this embodiment gasket member 30 is a compressible member located along both the interior and the exterior of expandable member 12.

Figure 21:
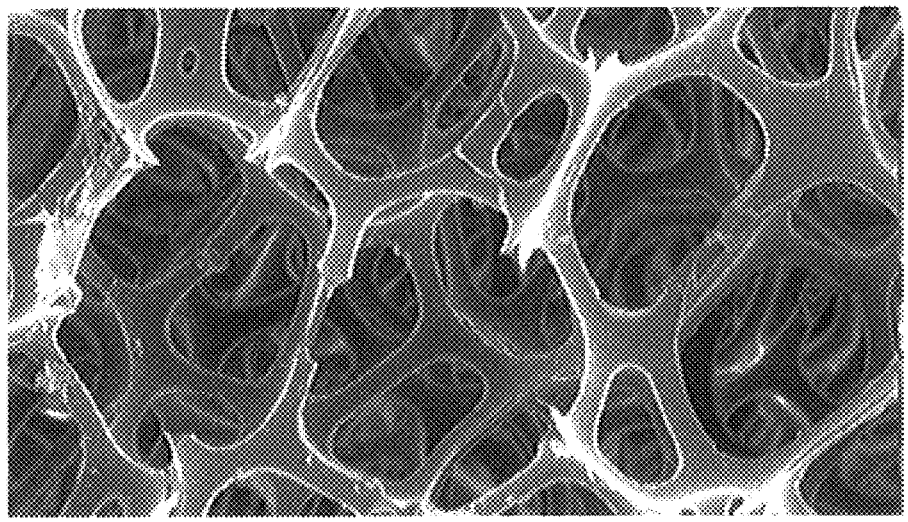
FIG. 21 is a photomicrograph of the gasket material prior to substantial cell ingrowth, as taken along section line 21—21 of FIG. 3.

Gasket member 30 can be made from any number of materials known to those skilled in the art. Preferably, gasket member 30 is made from an open cell polyurethane foam, however other flexible foams could be used, such as polyethylene, polytetrafluoroethylene, other various polymer materials which are woven or knitted to provide a flexible structure such as Dacron, polyurethane, polypropylene, polytetrafluoroethylene can also be used. Preferably, the polyurethane foam has a cell size of 50–100 pores per inch, and the density of the foam is 1.5–3.5 pounds per cubic foot. Foams having these qualities absorb the blood like a sponge, contributing to blood stagnation which leads to thrombosis. In addition, it provides a trellis for cellular infiltration, and eventually scaffolds tissue incorporation. This helps to better anchor the device within the body, thereby preventing stent migration. An example of such a foam is shown in the photograph of FIG. 21. FIG. 21 shows a scanning electron microscope of a open cell polyurethane foam having approximately 200–500 micrometer pores.

Figure 22:
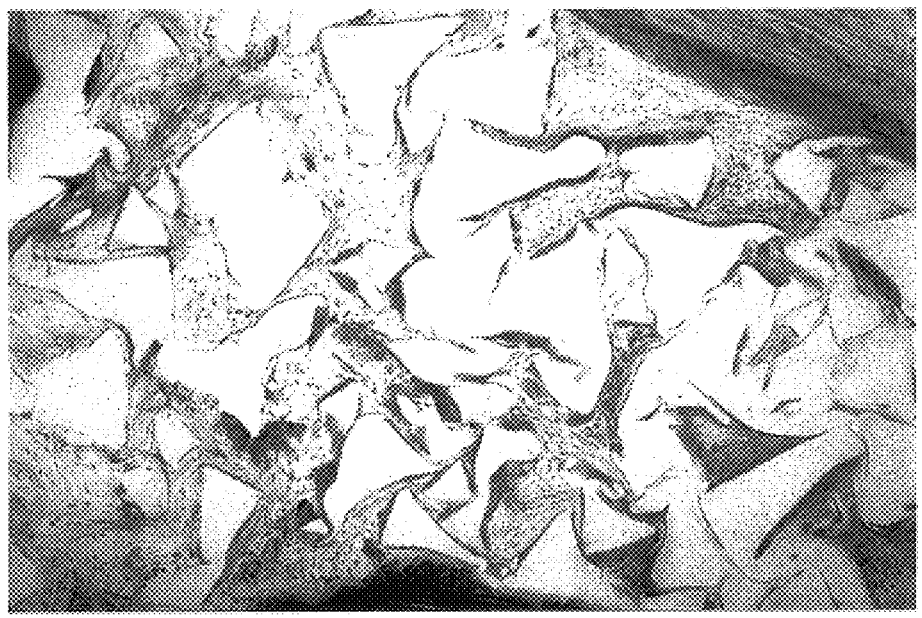
FIG. 22 is a photomicrograph of the gasket material after substantial cell ingrowth, or biofusion, has taken place as taken along line 22—22 of FIG. 19.

This ability of the tissue from the artery wall to incorporate the open-pore foam structure has been termed by assignee as "Biofusion". This tissue incorporation effect can best seen by referring to the photographs of FIGS. 21 and 22. FIG. 22 shows histological photographs of connective tissue infiltrating and healing into the gasket member 30 upon a 1 month follow-up of a device implanted into a target vessel. This ability of the tissue to heal into the foam creates a long term stable biological interface which, upon about six weeks after implantation, cannot be separated from the tissue without tearing the foam material. The "Biofusion" effect has many advantages. It has the potential to obviate late endo-leakage by preventing areas of non-organized clot from being displaced or recanalized. It is also believed that "Biofusion" creates a connective tissue collar around the gasket that would prevent the aortic neck from dilating over time. Restriction of neck dilation avoids endoleakage paths and implant migration that can be caused by an insufficient fit with the aorta. The use of such above described foams on stent-grafts is not limited to abdominal aortic aneurysm repair, but could be applied in many stent-graft applications such as other aneurysm repair and vessel malformation and occlusion.

The foams described above are preferably highly compressible, so as to keep the crimped profile low for better delivery. In addition, it is preferable that the gasket member be substantially impervious to the flow of blood, at least when in a partially compressed state. When used throughout for the present invention, materials which are substantially impervious to the flow of blood include materials which become substantially impervious to the flow of blood after being saturated with blood. When the stent tubes and graft members, described below, are inserted and expanded within the gasket 30, the gasket 30 will compress. In this state, the gasket should be substantially impervious to blood so as to prevent blood from flowing through the interior 18 of self-expanding member 12 and into the aneurysm. Gasket 30 can be attached to expandable self-expanding member 12 by any number of means including polyurethane glue, a plurality of conventional sutures of polypropylene, DACRON®, or any other suitable material and attached thereto. Other methods of attaching gasket 30 to the self-expanding member include adhesives, ultrasonic welding, mechanical interference fit and staples.

Figure 2:
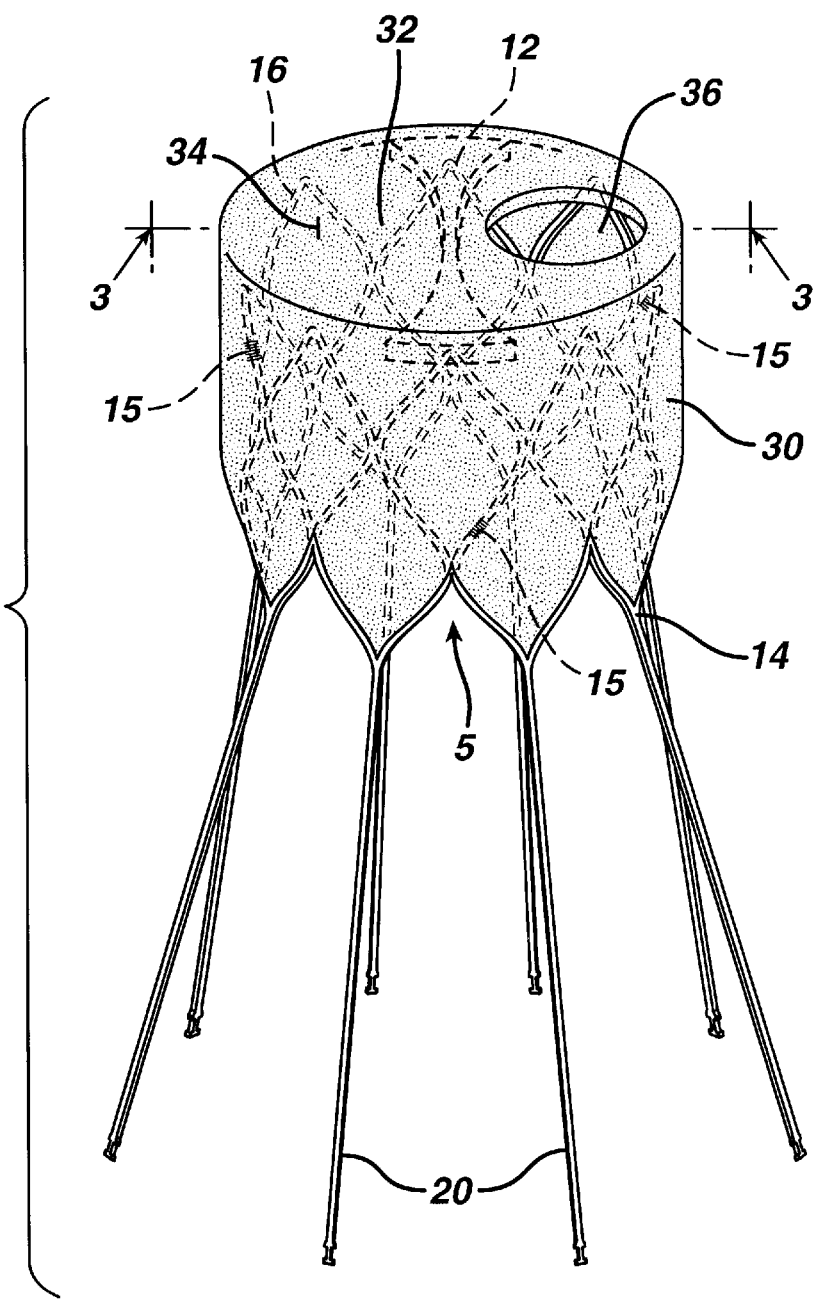
FIG. 2 is a view similar to that of FIG. 1 but including a gasket member made in accordance with the present invention.

As seen from FIG. 2, precursor stent 10 preferably includes a number of radiopaque markers 15. As shown, markers 15 are coils of radiopaque metal, wrapped around the struts of the stent. The markers are positioned along the stent so that the physician can better know the exact position of the stent during deployment when viewed under fluoroscopy. Markers 15 are preferably made from 0.010" diameter tantalum (Ta) wire wrapped tightly around the struts. Three markers are used; two near the distal end of the device, and one proximal thereto. The distal two are 180° apart, and the proximal one is equally spaced between the distal two when viewed from a rotation where the top two are spaced as far apart as possible. This proximal marker then aids proper rotational positioning of the device. Specifically, one of the distal markers is 5 mm long and is adjacent to the aperture 34 in the gasket; the other is 2 mm long and is adjacent to the hole 36. Since hole 36 should be placed adjacent to the right side of the aneurysm, as shown in FIG. 19, the small distal marker should be placed on the right side; the proximal marker (also 2 mm long) should appear fluoroscopically to be midway between the upper two markers.

Figure 3:
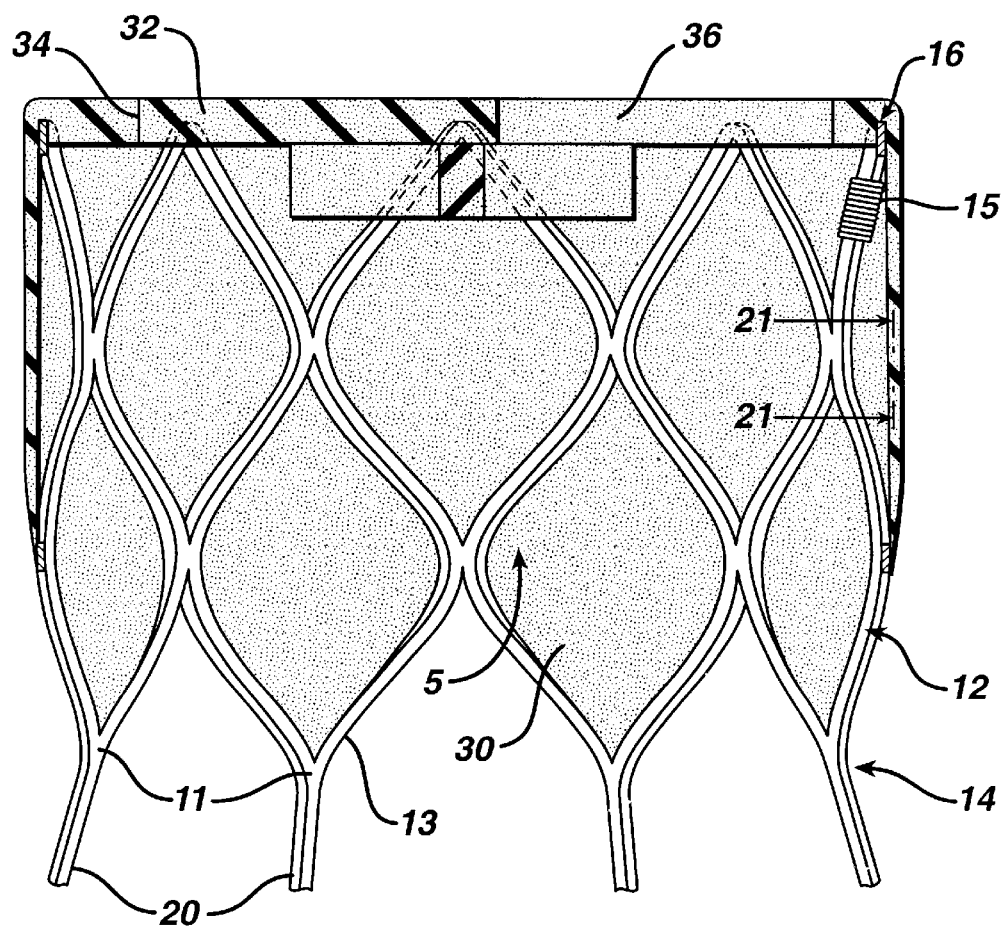
FIG. 3 is a cross-sectional view of the precursor stent of FIG. 2 taken along section line 3—3 of FIG. 2.

As seen from FIGS. 2 and 3, the precursor stent further includes an occlusive member 32 attached to self-expanding member 12. The occlusive member covers at least a portion of the interior of the expandable member. The occlusive member covers the interior of member 12 in such a way that a lumen 5 of the expandable member which provides passageway from its proximal end 14 to its distal 16 is at least partially blocked. Occlusive member 32 further includes two openings 34 and 36 extending therethrough. Opening 34 is relatively small and is designed to receive a guidewire, wherein such guidewire helps deliver precursor stent 10 to the target site. Opening 36 is relatively large, and is designed to receive another guidewire having a loaded stent-graft proximal thereto. As will be explained below, the occlusive member helps to ensure proper side by side placement of the two stent-grafts.

Figure 4:
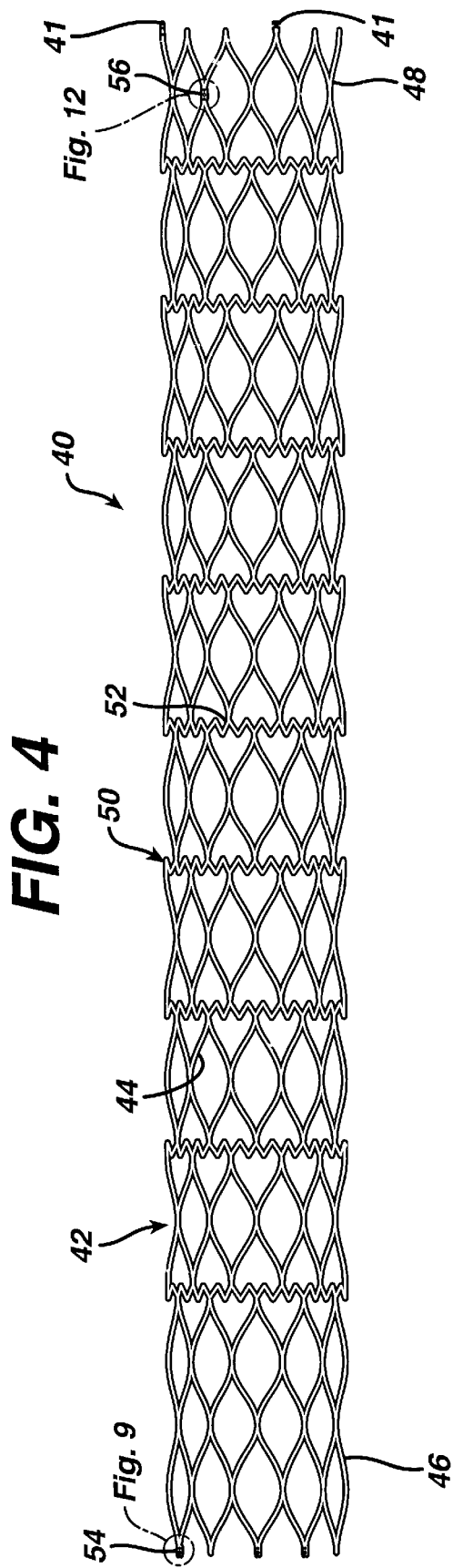
FIG. 4 is a side elevational view of an endograft stent prior to the application of the graft material and shown in an expanded state.

Precursor stent 10 acts to temporarily scaffold the gasket member within the body, until the stent-grafts are deployed (see FIG. 19). Shown in FIG. 4 is a preferred embodiment of a stent 40 for use in a stent-graft in accordance with the present invention. Stent 40 is made from a plurality of interconnected struts 44, and has an interior surface 43A and an exterior surface 43B (shown in FIG. 15). FIG. 4 shows stent 40 in its fully deployed, un-crimped state. As will be appreciated by those skilled in the art, stent 40 should be crimped to a smaller diameter prior to insertion into a patient. Stent 40 is preferably made from superelastic Nitinol, and have enough outward force to stay within the body, without the use of the precursor stent 10. Stent 40 is preferably made from a single tube of Nitinol, having the following features laser cut therein. Stent 40 has a number of hoops 42 comprising a number of struts 44 making a diamond shape configuration, wherein each hoop preferably has 9 diamonds. Stent 40 further includes a number of sinusoidal rings 50 for connecting adjacent hoops to one another. The sinusoidal. rings are made from a number of alternating struts 52, wherein each ring preferably has 54 struts. As will be explained in detail below in connection with the discussion of FIGS. 9–14, stent 40 includes a distal attachment means 54 and a proximal attachment means 56.

Stent 40 has a proximal hoop 48 and a distal hoop 46, also referred to as anchors. The proximal hoop is flared, and is exposed after the graft has been attached thereto. The diamond pattern for the anchors, as well as the other hoops, provide the hoops with radial and longitudinal stiffness. The longitudinal strength provides for better mechanical fixation of stent 40 to a graft (described below). The radial strength provides the distal hoop 46 with better attachment and sealing to stent gasket or precursor stent 10, and provides the proximal hoop 48 with better fixation and sealing to the arterial wall. In one preferred embodiment, the proximal and distal hoops have greater radial and longitudinal strength than the hoops therebetween. This creates a stent-graft having stiff ends for anchoring, but a more flexible body for navigation through the vasculature. The stiffer ends can be accomplished by changing the dimensions of the struts for the end hoops, or by varying the heat treatment of the end hoops during manufacture. The rings allow the stent to bend more easily, and generally provide for more flexibility when the stent is being delivered through a tortuous vessel. When a non-compliant graft is attached to stent 40, the strength of the diamond hoops scaffolds any graft folding into the blood flow lumen, while maintaining a tight kink radius.

Figure 5:
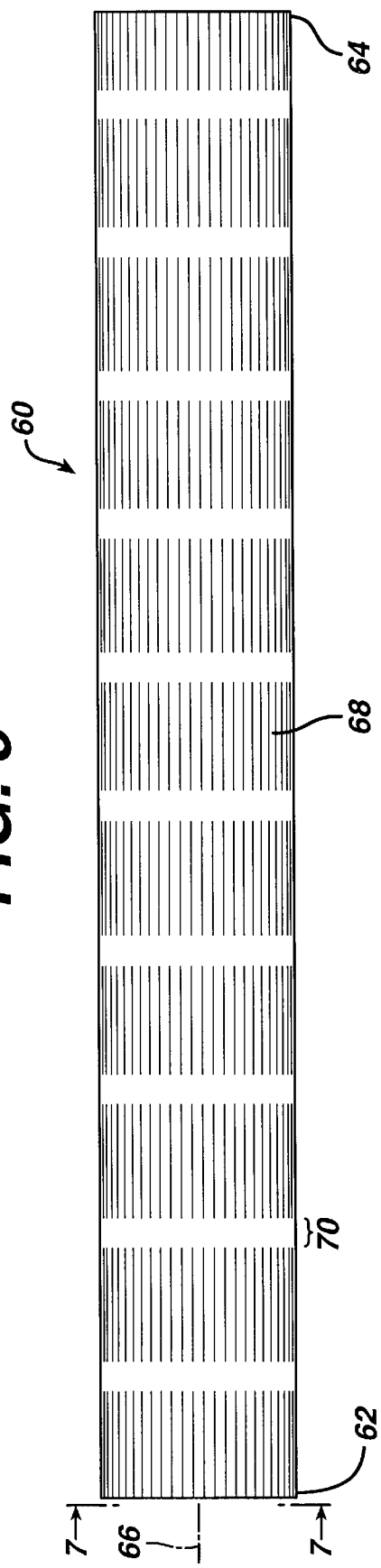
FIG. 5 is a side elevational view of a longitudinally pleated graft to be used in conjunction with the stent of FIG. 4 wherein the pleats are discontinuous.
Figure 6:
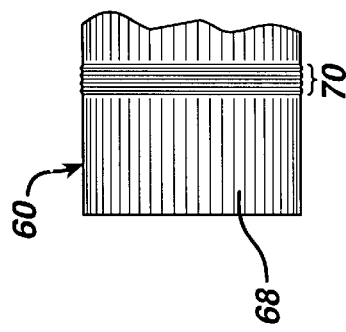
FIG. 6 is a partial side elevational view of another embodiment of the graft wherein the longitudinal pleats are interrupted by circumferential pleats.
Figure 7:
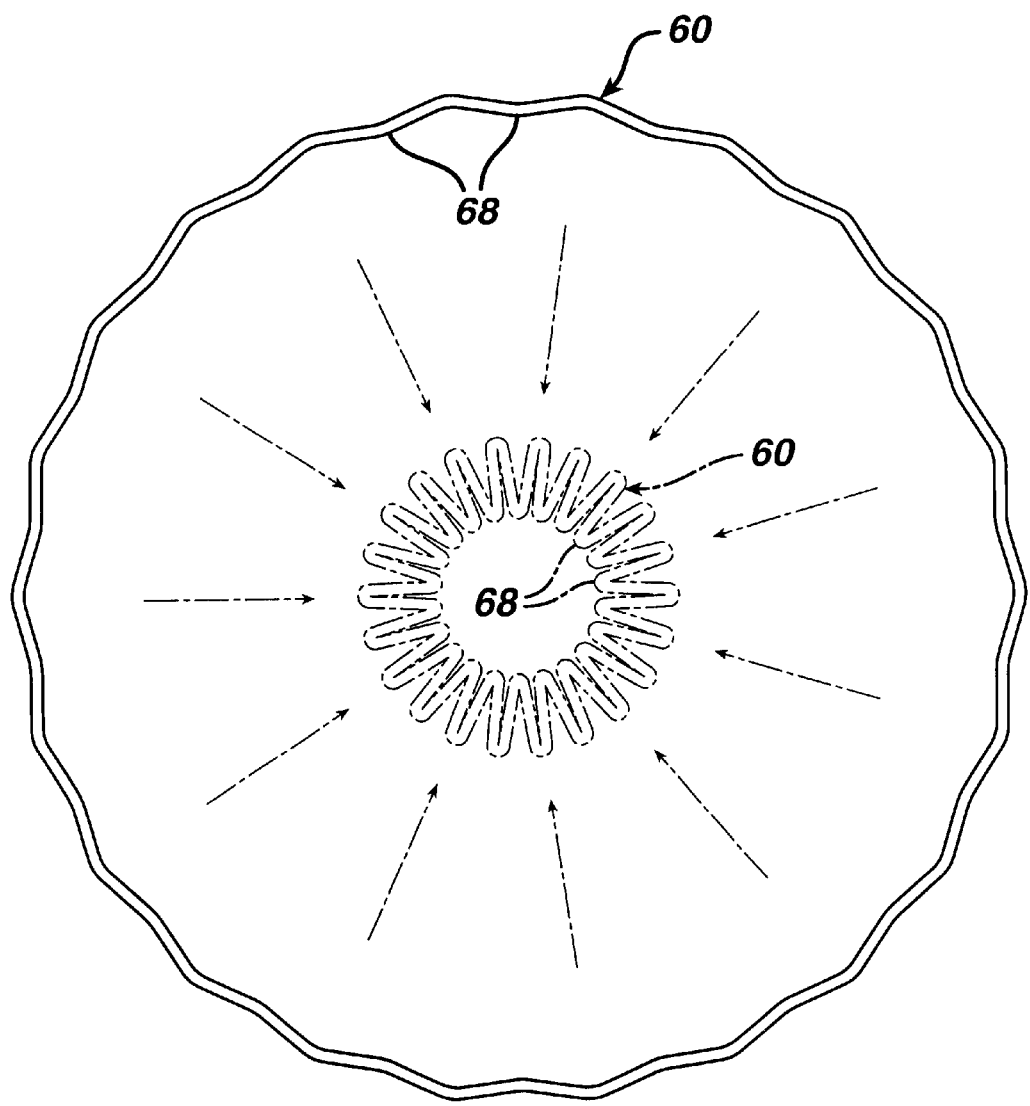
FIG. 7 is an end elevational view of the graft as taken along view line 7—7 of FIG. 5, the broken line work representing the graft in a compressed state.

As stated above, stent 40 preferably has a graft member attached thereto. The graft member covers at least a portion of the interior or exterior of stent 40, and most preferably covers substantially all of said exterior of said stent 40 Shown in FIGS. 5–7 is an embodiment of a tubular graft 60 for use with the present invention. Graft member 60 can be made from any number of materials known to those skilled in the art, including woven polyester, Dacron, Teflon or polyurethane. Graft 60 has a proximal end 64, a distal end 62, and a longitudinal axis 66 extending therebetween. As seen from FIG. 5, graft 60 has a plurality of longitudinal pleats 68 extending along its surface, and being generally parallel to longitudinal axis 66. As seen from FIG. 7, when the graft 60 is collapsed around its center, much as it would be when it is delivered into a patient, the pleats in the graft come together as a series of radially oriented regular folds which pack together efficiently, so as to minimize wrinkling and other geometric irregularities. Upon subsequent expansion, graft 60 assumes its natural cylindrical shape, and the pleats or folds uniformly and symmetrically open.

The pleats provide for a more uniform crimping of the graft 60, which helps the assembled stent graft (stent 40 attached to graft 60, as will be discussed below) to crimp into a relatively low profile delivery system, and provides for a controlled and consistent deployment therefrom. In addition, pleats 68 help facilitate stent graft manufacture, in that they indicate the direction parallel to the longitudinal axis, allowing stent to graft attachment along these lines, and thereby inhibiting accidental twisting of the graft relative to the stent after attachment. The force required to push the stent-graft out of the delivery system may also be reduced, in that only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

In one preferred embodiment, the depths of pleats 68 range from 0.06 inch to 0.07 inch for a graft having a crimped inner diameter of 0.08 inch and a crimped outer diameter ranging from 0.131 inch to 0.155 inch. This combination of pleat depth and inner and outer diameters results in pleat frequencies that generally preclude the existence of excessive radial graft flaps across the range of diameters for the device.

As seen best from FIG. 6, graft 60 preferably includes a plurality of radially oriented pleat interruptions 70. The pleat interruptions are substantially circular and are oriented perpendicular to longitudinal axis 66. While the pleats 68 mentioned above provide for a uniform crimping of graft 60, they may tend to increase kink propensity since they run perpendicular to the graft's natural folding tendencies when bent along its axis. Pleat interruptions 70 allow the graft to better bend at selective points. This design provides for a graft that has good crimpability and improved kink resistance.

Figure 9:
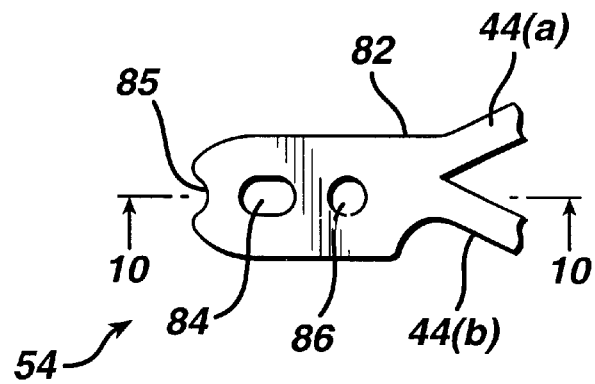
FIG. 9 is an enlarged partial plan view of an attachment tab at the cranial end of the stent as shown in the encircled area of FIG. 4.
Figure 10:
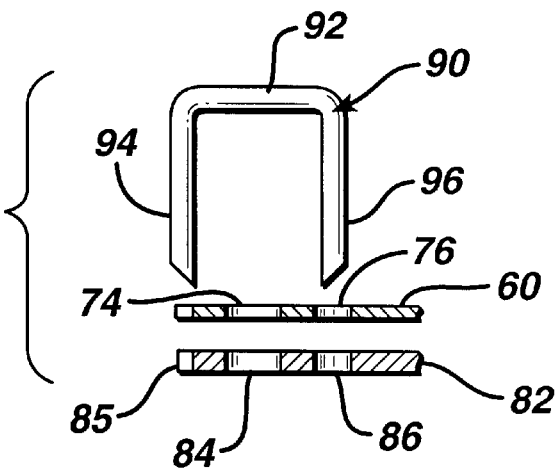
FIG. 10 is a partial, exploded cross-sectional view of the attachment tab as taken along section line 10—10 of FIG. 9 and includes a staple and a portion of the graft material prior to affixing the graft to the stent.
Figure 11:
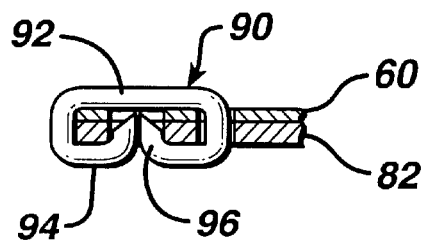
FIG. 11 is a partial cross-sectional view of the attachment means after crimping the staple.

FIG. 9 shows an up-close view of distal attachment means 54 of stent 40. Distal hoop 46 of stent 40 has a plurality of attachment tabs 82 extending therefrom which are formed from the joining together of two struts 44(*a*) and 44(*b*). Attachment means 54 comprises two apertures 84 (first aperture) and 86 (second aperture) extending therethrough. As seen from FIG. 10, graft 60 also preferably includes two apertures 74 and 76 (which can be initially created during the attachment process) which are coextensive with apertures 84 and 86 when graft 60 is placed over stent 40 for attachment. Finally, attachment means 54 includes a staple 90 having a crown 92 and attachment legs 94 (first leg) and 96 (second leg) extending therefrom. Attachment leg 96 extends through apertures 76 and then aperture 86. Simultaneously, leg 94 bends around notch 85, but it does not penetrate graft 60 like leg 96. Thereafter, attachment leg 94 and 96 are bent back through apertures 84 and 74 and in towards crown 92, so as to attach the distal end of the graft to the distal end of the stent as shown in FIG. 11. Legs 94 and 96 make contact with crown 92 after attachment. Preferably, there are six staples at the distal end.

Figure 12:
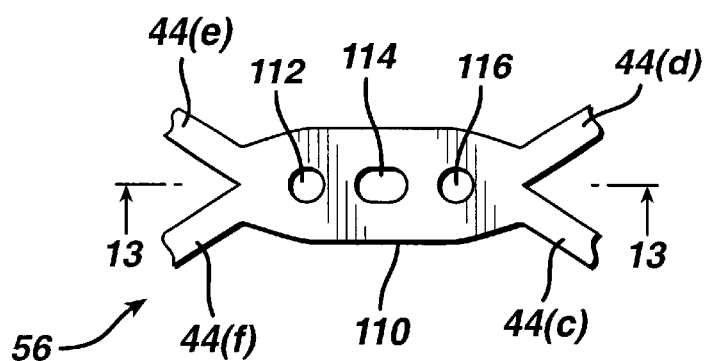
FIG. 12 is an enlarged partial plan view of an attachment node at the caudal end of the stent as shown in the encircled area of FIG. 4.
Figure 13:
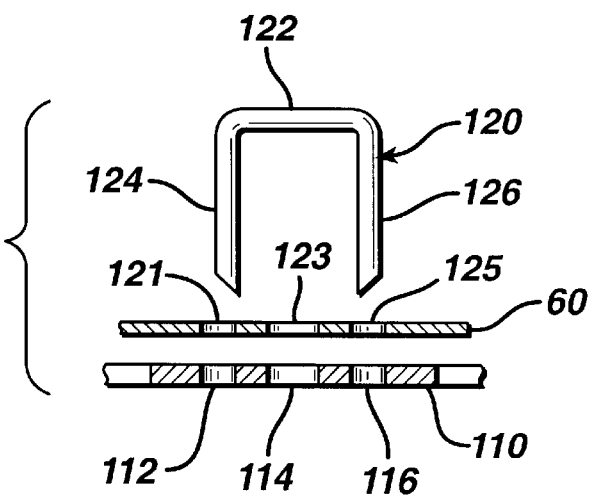
FIG. 13 is a partial, exploded cross-sectional view of the attachment node as taken along section line 13—13 of FIG. 12 and includes a staple and a portion of the graft material prior to affixing the graft to the stent.
Figure 14:
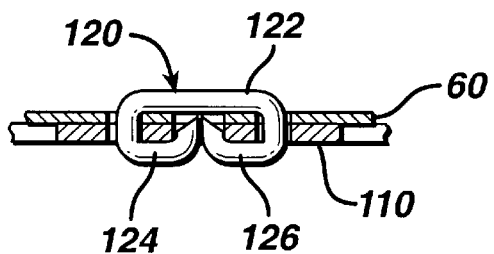
FIG. 14 is a partial cross-sectional view of the attachment means after crimping the staple.

FIG. 12 shows an up-close view of proximal attachment means 56 of stent 40. Proximal hoop 48 of stent 40 has a plurality of members 110 occurring at the joining of four struts 44(*c*)–44(*f*). Attachment means 56 comprises three apertures 112 (first aperture), 114 (middle aperture) and 116 (second aperture) extending therethrough. As seen from FIG. 13, graft 60 also preferably includes three apertures 121, 123 and 125 (which can be initially made during the attachment process by puncturing therethrough with a staple) which are coextensive with apertures 112, 114 and 116 when graft 60 is placed over stent 40 for attachment. Finally, attachment means 56 includes a staple 120 having a crown 122 and legs 124 (first leg) and 126 (second leg) extending therefrom. Legs 124 and 126 extend through apertures 112 and 116 and then through apertures 121 and 125 respectively. Thereafter, legs 124 and 126 are bent back through apertures 124 and 114 and in towards crown 122, so as to attach the proximal end of the graft to the proximal end of the stent as shown in FIG. 14. Legs 124 and 126 make contact with crown 122 after attachment. Preferably, there are three staples at the proximal end.

The above staple aperture design has many advantages for attaching a stent to a graft. Because the legs of the staple are folded around and imbedded within a pocket or the like, any risk of puncturing an inflation balloon is minimized. In addition, the structural integrity of the stent-graft is believed to be increased in that these staples should more securely attach the graft to the stent compared to prior art designs which use suture or adhesives to attach the graft to the stent. Staples 90 and 120, illustrated in FIG. 8, can be made from any number of materials known in the art, including tantalum alloys, platinum alloys or stainless steel, such as 316 LVM stainless steel. The staples may take on other configurations and shapes, and can be coated for lubricty purposes. Having the staples made from a radiopaque material helps the physician in accurately deploying the device.

Figure 8:
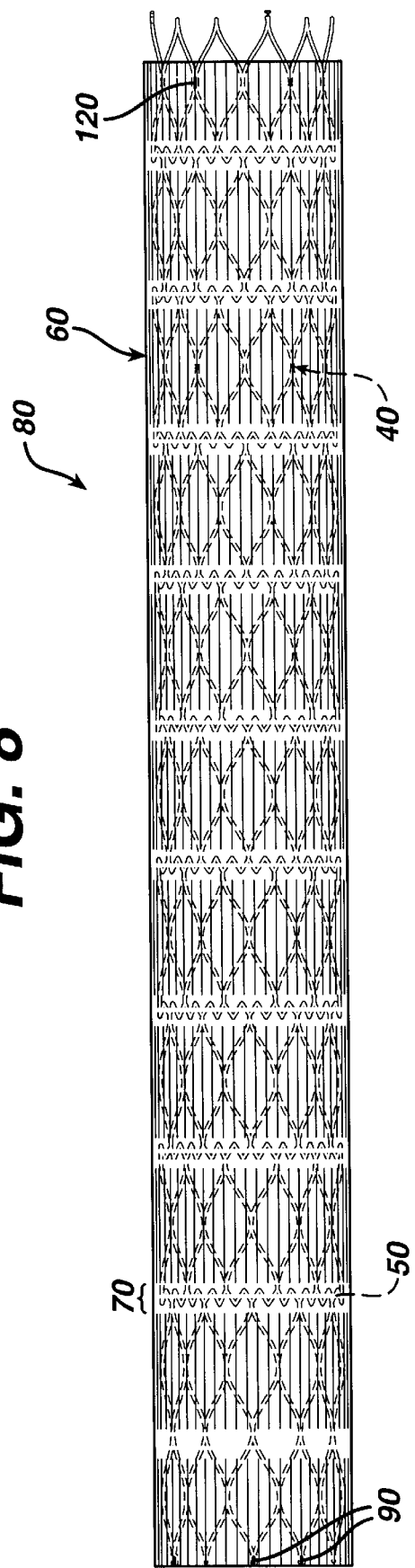
FIG. 8 is a side elevational view of a complete stent-graft assembly shown in a deployed state.
Figure 15:
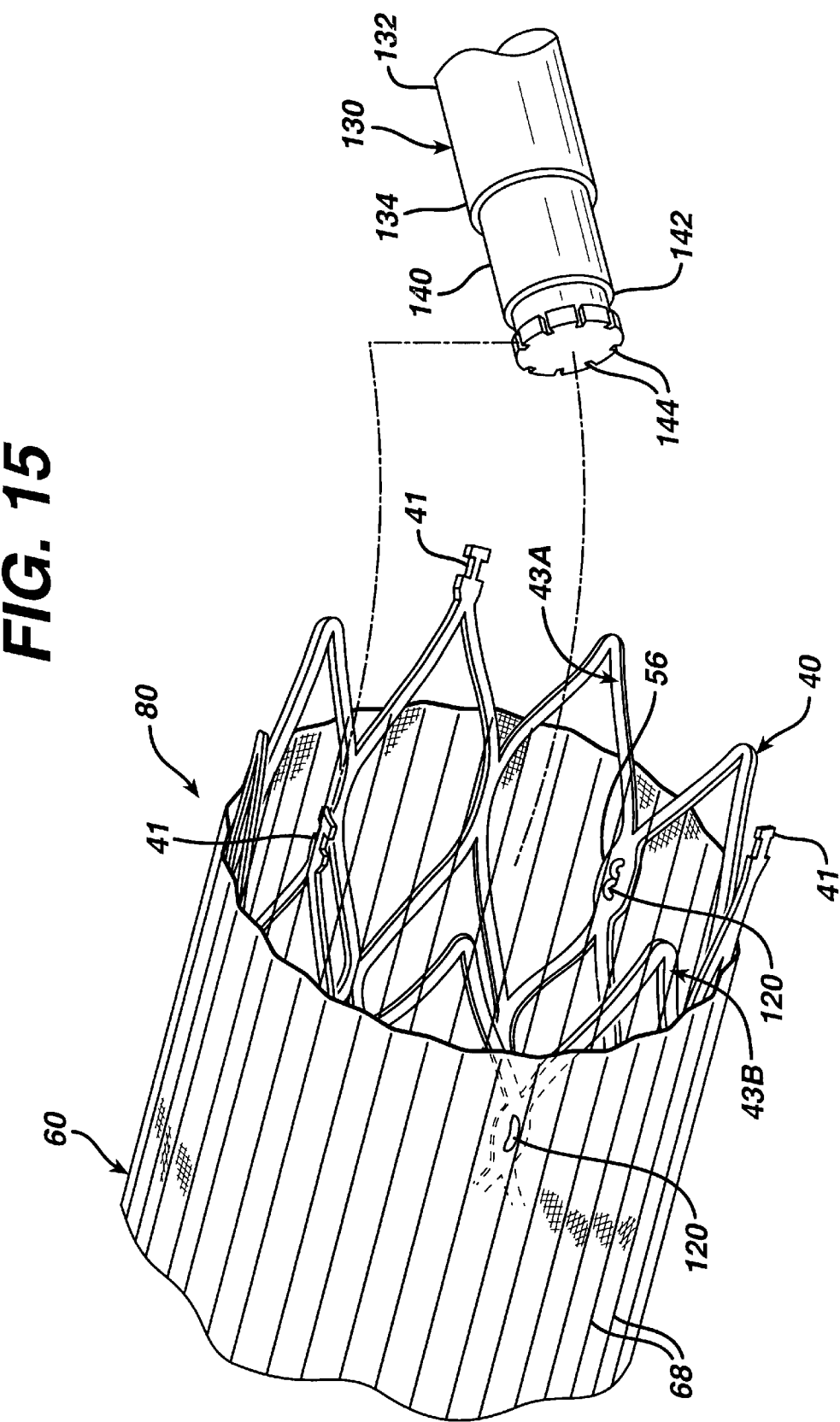
FIG. 15 is a partial, exploded perspective view of the caudal end of the stent-gasket, or endograft, and a portion of the delivery system shown after its release from the delivery system.

Another feature of stent-graft 80, illustrated in FIG. 8, can be better understood by referring to its delivery apparatus 130 shown in FIG. 15. Apparatus 130 is very similar to other self-expanding delivery apparatus described in the above incorporated references. Apparatus 130 includes an outer sheath 132 which is essentially an elongated tubular member, similar to ordinary guiding catheters which are well known to those of ordinary skill in the art. An example of a particularly preferred outer sheath is described in commonly assigned U.S. Pat. No. 6,019,778 issued on Feb. 1, 2000, which is hereby incorporated herein by reference. Sheath 132 has a distal end 134 and a proximal end (not shown). Apparatus 130 also includes an inner shaft 140 located coaxially within the outer sheath 132 prior to deployment. The inner shaft has a distal end 142 and a proximal end (not shown). The distal end 142 of the shaft has at least two grooves 144 disposed thereon. Stent 40 preferably has a number of flanges 41 disposed at its proximal end. The flanges on the stent are set within the grooves of the inner shaft, thereby releasably attaching the stent to the inner shaft. The delivery system for precursor stent 10 is also similar, having an outer sheath and an inner shaft wherein the shaft has grooves to receive flanges 28 of precursor stent 10.

The advantages of flanges 41 on stent 40 and flanges 28 on precursor stent 10 and the grooves on the inner shafts of their delivery system is that they may allow for partial deployment of the stents and recapture within the delivery apparatus if the physician is not pleased with the position of the stent. The present invention allows the physician to partially deploy one of the stents (precursor stent 10 or stent-graft 80) while the flanges remain within the sheath. The flange groove combination allows the physician to "pull" the stent back into the delivery device if the placement is not optimal.

Figure 23:
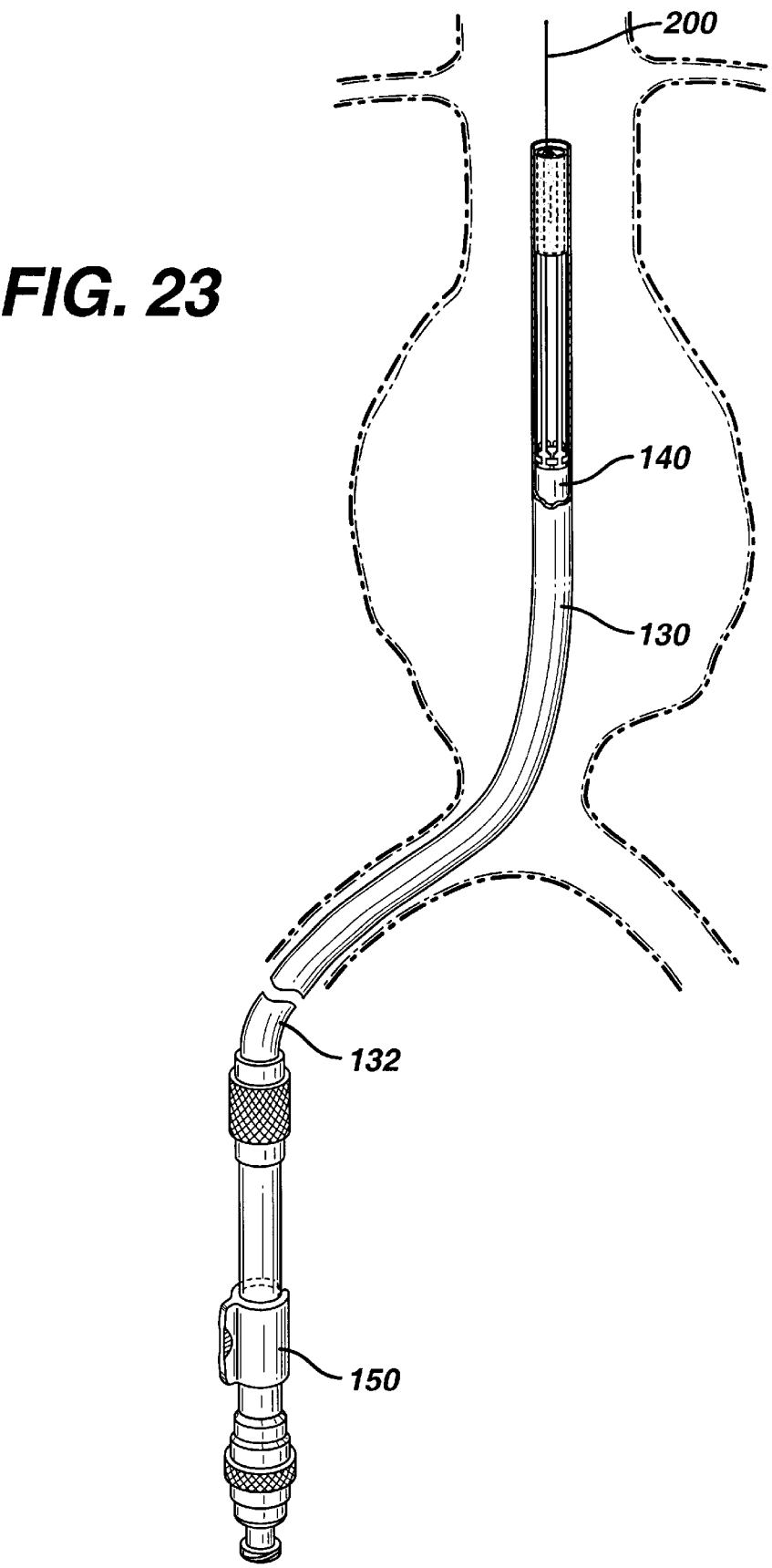
FIG. 23 is an elevational view of a delivery system for a stent gasket made in accordance with the present invention, wherein the delivery system is inserted into an abdominal aortic aneurysm.
Figure 25:
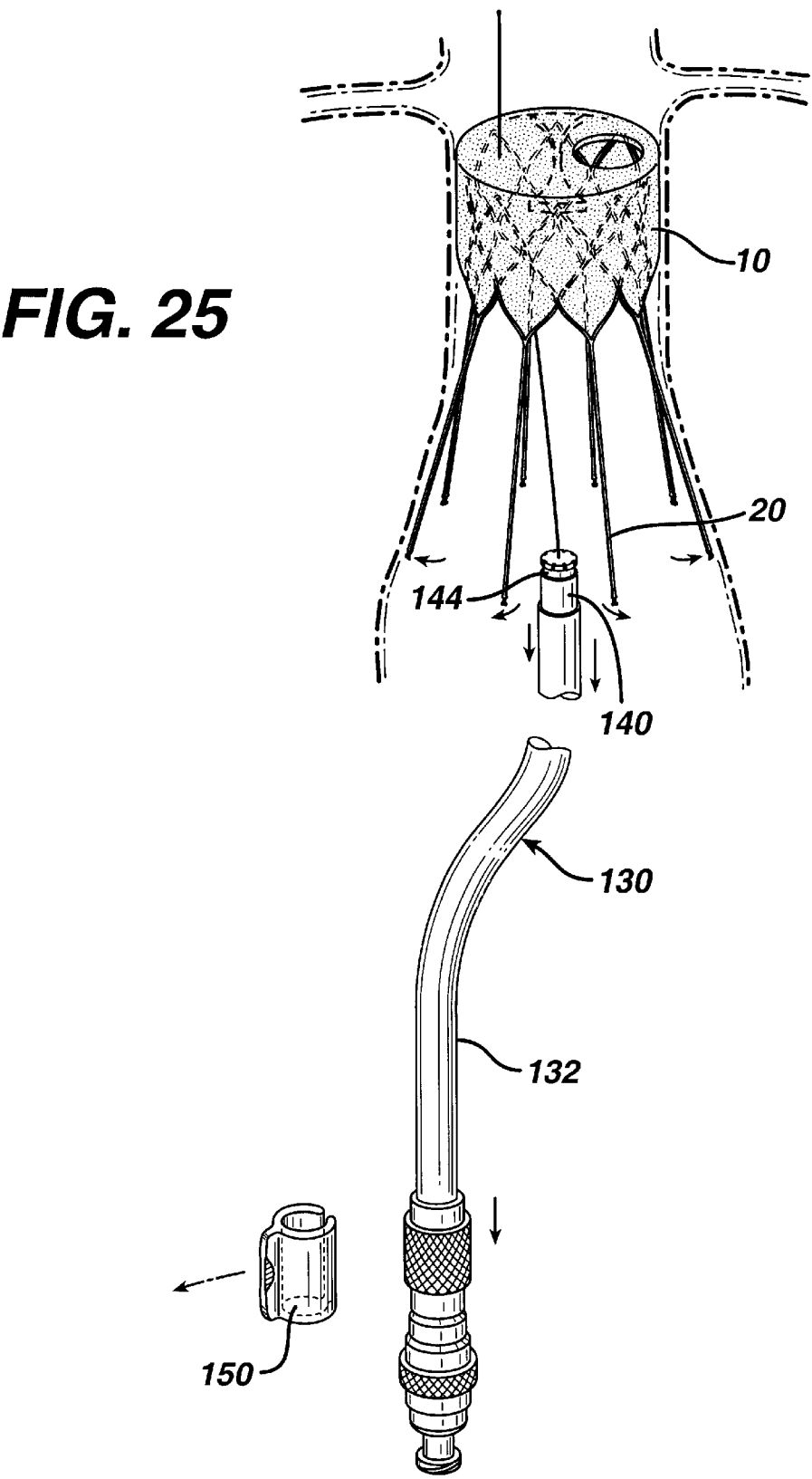
FIG. 25 is a view similar to that of FIG. 24 but showing the stent gasket fully deployed from its delivery system.

The advantages of flanges 28 on precursor stent 10 and the grooves on the inner shafts of their delivery system can best be described by referring to FIGS. 23–25. FIG. 23 shows an exemplary embodiment of the delivery apparatus 130 for stent gasket or precursor stent 10. Apparatus 130 is very similar to other self-expanding delivery apparatus described in the above incorporated references. Apparatus 130 includes an outer sheath 132 which is essentially an elongated tubular member, similar to ordinary guiding catheters which are well known to those of ordinary skill in the art. An example of a particularly preferred outer sheath is described in commonly assigned U.S. Pat. No. 6,019,778 issued on Feb. 1, 2000, which is hereby incorporated herein by reference. Apparatus 130 also includes an inner shaft 140 located coaxially within the outer sheath 132 prior to deployment. Inner shaft 140 includes a number of grooves 144. As seen from FIG. 24, this arrangement allows for partial deployment of precursor stent 10 and recapture within the delivery apparatus if the physician is not pleased with the initial position of the stent. The present invention allows the physician to partially deploy precursor stent 10 while the flanges remain within the sheath. The flange groove combination allows the physician to "pull" the stent back into the delivery device if the placement is not optimal.

In order to prevent the physician from prematurely completely deploying the precursor stent 10, a releasable stop 150 is preferably placed on the inner shaft. The stop could be a ring having a greater diameter than the sheath, so that as the sheath is pulled proximally along the inner shaft it hits the stop, and prevents full deployment of the entire precursor stent 10. The stop is preferably releasably attached to the inner member so that it can be released from its engagement with the inner shaft to allow the outer member to slide back enough to fully deploy the entire precursor stent 10 within the body.

Figure 16:
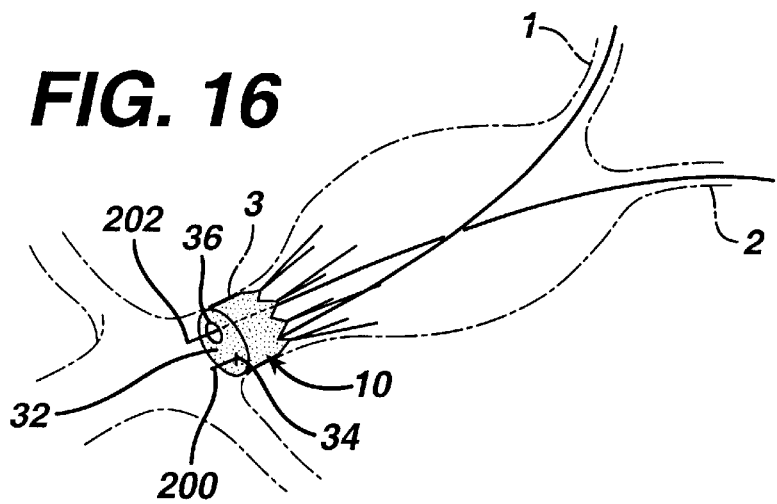
FIGS. 16, 17 and 18 are sequential schematic perspective views showing the method of positioning and deploying the stent-grafts, or endografts, after the precursor stent has already been deployed.
Figure 17:
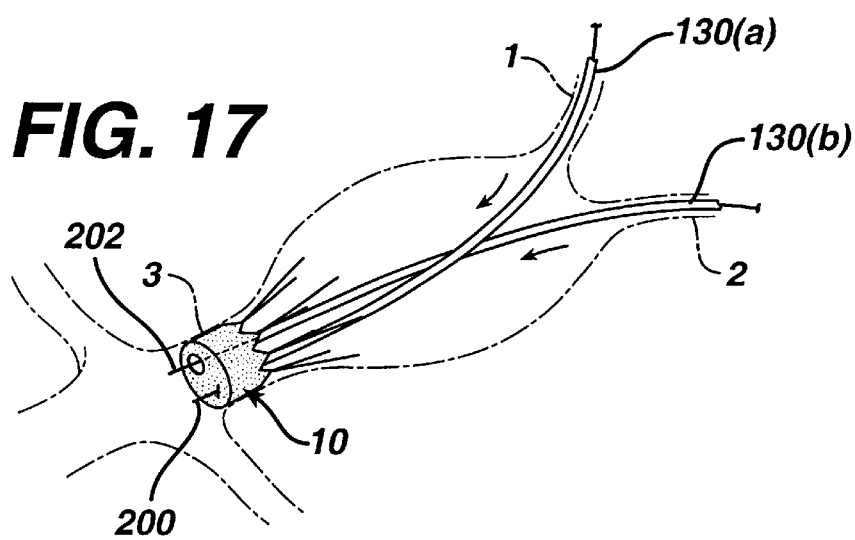
Figure 18:
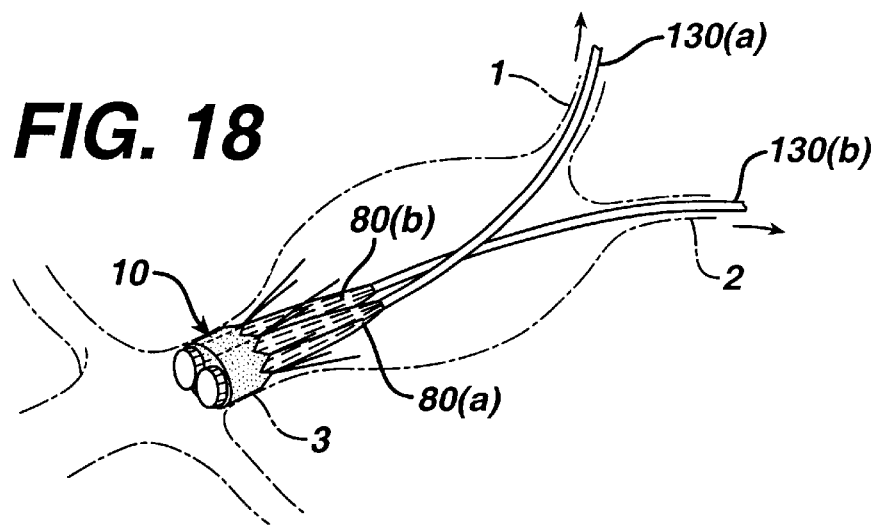

FIGS. 16–18 generally show how the above described invention is deployed within the body. Prior to what is shown in FIG. 16, the physician would first insert the precursor stent 10, having the gasket member attached thereto, into the body with the aid of guidewire 200, which remains in the body after deployment. The stent gasket is delivered through one of the patient's femoral arteries and into a first iliac artery 1 and deployed within the infrarenal neck 3. Thereafter, the delivery device for the precursor stent 10 is removed, without removing guidewire 200, and another guidewire 202 is inserted through the other femoral artery and into the other iliac artery 2. Because the size of opening 36 in occlusive member 32 is relatively large, the physician can only maneuver guidewire 202 therethrough. Thereafter stent-graft delivery apparatus 130(a) and 130(b) are inserted into femoral arteries and into the iliac arteries 1 and 2 by sliding them over guidewires 200 and 202, and accurately delivering them to the target site. Thereafter, both stent-grafts 80(a) and 80(b) are either separately or simultaneously deployed within the body. Ultimately the distal ends of the stent-grafts reside level with each other, just below the renal arteries, and some distance above the distal end of the stent gasket. The bodies of the stent-grafts pass through the stent gasket and through the aneurysm sac.

Figure 20:
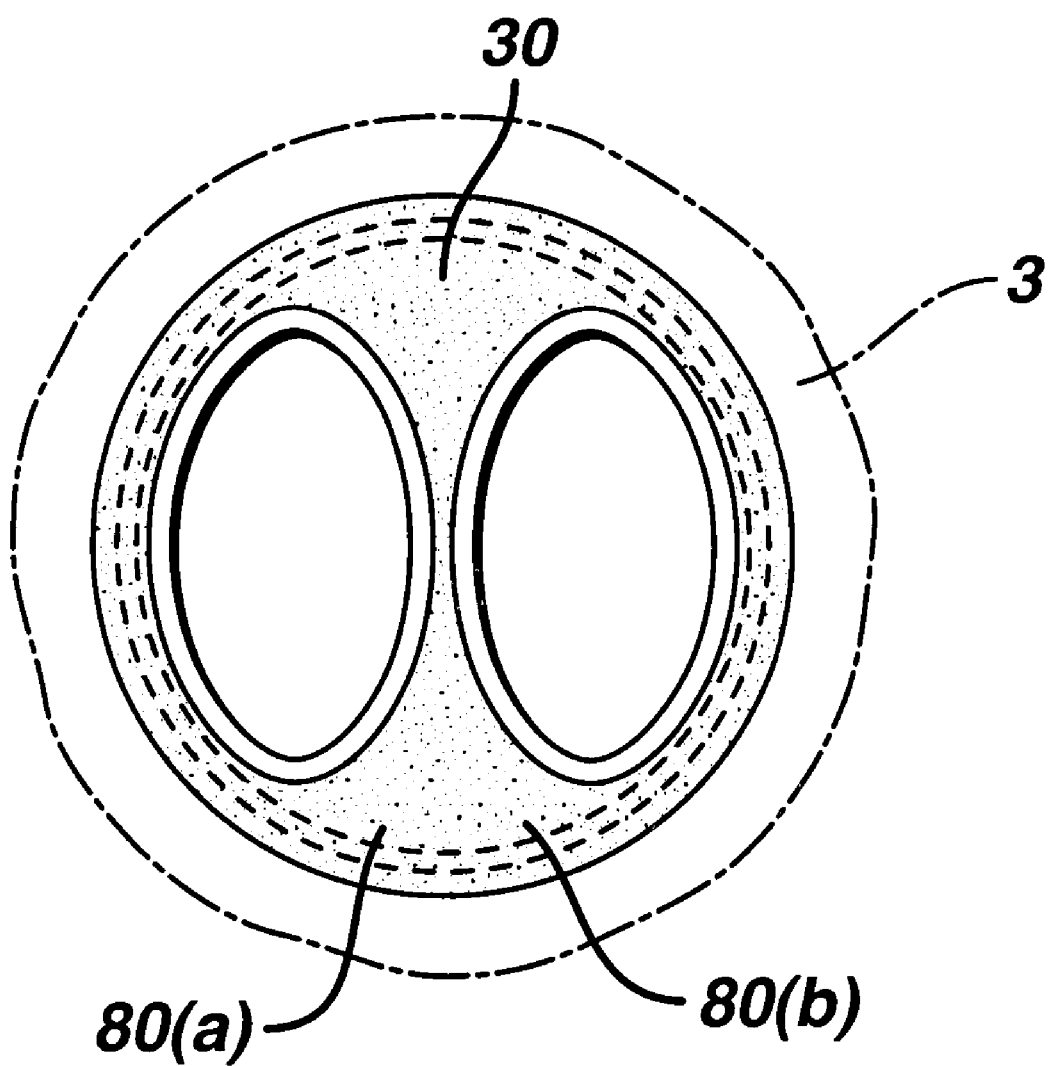
FIG. 20 is a top plan view of the precursor stent as seen along view line 20—20 of FIG. 19.

After properly delivery, precursor stent 10 and stent-grafts 80(a) and 80(b) should appear as they do in FIG. 19. Precursor stent 10 along with its attached gasket member 30 are firmly secured within the infrarenal neck 3. The outward force of the stent-grafts 80 on the precursor stent 10 help to secure the device within the body. The proximal ends of the stent-grafts are firmly attached to the iliac arteries 1 and 2. Thereafter blood will flow from the abdominal aorta 302 down into and through stent-grafts 80(a) and 80(b) and into iliac arteries 1 and 2, thereby bypassing the aneurysmal sack 304. If all the components are placed accurately, distal end of the device should appear as it does in FIG. 20.

In order to prevent the physician from prematurely completely deploying the precursor stent 10, a releasable stop is preferably placed on the inner shaft. The stop could be a ring having a greater diameter than the outer member, so that as the outer member is pulled proximally along the inner shaft it hits the stop, and prevents full deployment of the entire precursor stent 10. The stop is preferably releasably attached to the inner member, by threads, snap fit or the like, so that it can be released from its engagement with the inner shaft to allow the outer member to slide back enough to fully deploy the entire precursor stent 10 within the body.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. A stent-graft for insertion into a body lumen in order to repair said lumen, said stent-graft comprising:
    a. a substantially cylindrical hollow expandable stent comprising a plurality of interconnected struts, said stent having a distal end and a proximal end, and an interior surface and an exterior surface, at least one strut of said stent having adjacent first and second apertures extending therethrough from said interior surface to said exterior surface;
    b. a graft member covering a predetermined portion of least one of said interior surface and said exterior surface; and
    c. a staple attaching said graft member to said stent, said staple comprising a crown and two legs extending therefrom, at least one of said legs extending through said graft material and through said first aperture, both of said legs being bent towards said crown such that said legs extend through said second aperture.

2. The stent-graft according to claim 1, wherein said graft member covers substantially all of said exterior surface of said stent.

3. The stent-graft according to claim 1 wherein said stent is a self-expanding stent.

4. The stent-graft according to claim 3 wherein said stent is made from a superelastic nickel titanium alloy.

5. The stent-graft according to claim 1 wherein said graft member is selected from a group of materials consisting of Dacron, Teflon, woven polyester, and polyurethane.

6. The stent-graft according to claim 1 wherein said staple is radiopaque.

7. A stent-graft for insertion into a body lumen in order to repair said lumen, said stent-graft comprising:
    a. a substantially cylindrical hollow expandable stent comprising a plurality of interconnected struts, said stent having a distal end and a proximal end, and an interior surface and an exterior surface;
    b. a graft member covering a predetermined portion of least one of said interior surface and said exterior surface;
    c. a tab extending from at least one of said struts at one of said ends of said stent, said tab having adjacent first and second apertures extending therethrough; and
    d. a staple attaching said graft member to said stent, said staple comprising a crown and first and second legs extending therefrom, said first leg extending through said graft material and through said first aperture, both of said legs being bent towards said crown such that said legs extend through said second aperture.

8. The stent-graft according to claim 7, wherein said graft member covers substantially all of said exterior surface of said stent.

9. The stent-graft according to claim 7 wherein said stent is a self-expanding stent.

10. The stent-graft according to claim 9 wherein said stent is made from a superelastic nickel titanium alloy.

11. The stent-graft according to claim 7 wherein said graft member is selected from a group of materials consisting of Dacron, Teflon, woven polyester, and polyurethane.

12. The stent-graft according to claim 7 wherein said tab further includes a notch at an end most portion of said tab, wherein said second leg of said staple abuts against and bends around said notch.

13. The stent-graft according to claim 7 wherein said staple is radiopaque.

14. A stent-graft for insertion into a body lumen in order to repair said lumen, said stent-graft comprising:
   a. a substantially cylindrical hollow expandable stent comprising a plurality of interconnected struts, said stent having a distal end and a proximal end, and an interior surface and an exterior surface, at least one of said struts having adjacent first, second and middle apertures extending therethrough;
   b. a graft member covering a predetermined portion of at least one of said interior surface and said exterior surface;
   c. a staple attaching said graft member to said stent, said staple comprising a crown and first and second legs extending therefrom, said first leg extending through said graft material and through said first aperture, said second leg extending through said graft material and through said second aperture, both of said legs being bent towards said crown such that said legs extend through said middle aperture.

15. The stent-graft according to claim 14, wherein said graft member covers substantially all of said exterior surface of said stent.

16. The stent-graft according to claim 14 wherein said stent is a self-expanding stent.

17. The stent-graft according to claim 16 wherein said stent is made from a superelastic nickel titanium alloy.

18. The stent-graft according to claim 14 wherein said graft member is selected from a group of materials consisting of Dacron, Teflon, woven polyester, and polyurethane.

19. The stent-graft according to claim 14 wherein said staple is radiopaque.

* * * * *